(12) United States Patent
Brindavanam et al.

(10) Patent No.: US 6,599,541 B1
(45) Date of Patent: Jul. 29, 2003

(54) COMPOSITION FOR TREATMENT OF DRUG RESISTANT BACTERIAL INFECTIONS AND A METHOD OF TREATING DRUG RESISTANT BACTERIAL INFECTIONS

(75) Inventors: Narasimha Baba Brindavanam, Ghaziabad (IN); Chandra Kant Katiyar, Ghaziabad (IN); Dasalukunte Bhimrao Ananta Narayana, Ghaziabad (IN)

(73) Assignee: Dabur Research Foundation, Utter Pradesh (IN)

( * ) Notice: Subject to any disclaimer, the term of this patent is extended or adjusted under 35 U.S.C. 154(b) by 0 days.

(21) Appl. No.: 09/662,809

(22) Filed: Sep. 15, 2000

(30) Foreign Application Priority Data

Sep. 17, 1999 (IN) ............................. 1260/D/99

(51) Int. Cl.⁷ .................... A61K 35/78; A01N 25/34
(52) U.S. Cl. .................. 424/761; 424/404; 424/774; 424/779; 424/775; 424/725
(58) Field of Search .............. 424/404, 195.1, 424/725, 761, 775, 779, 777, 778; 549/348, 381; 514/450

(56) References Cited

U.S. PATENT DOCUMENTS 5,856,526 A * 1/1999 Sankaram et al. .......... 549/348

OTHER PUBLICATIONS

Willimams et al. The Inhibitor Effect of Azadirachtin on *Bacillus subtilis, Escherichia coli* and Paenibacillus Larvae, The Causative Agent of American Foulbrood in the Honeybee, Apis Mellifera L.: 1998, Journal of Invertebrate Pathology 72, pp. 252–257.*

H. S. Puri, "NEEM. The Divine Tree," Chemical Constituents, pp. 24–26, Harwood Academic Publishers, The Netherlands, (1999).

Dr. D. N. Tewari , "Chemistry of NEEM," Monograph on NEEM, pp. 147–171, International Book Distributors, Dehra Dun, India, (1992).

The Merck Index, an Encyclopedia of Chemicals, Drugs and Biologicals, Merck Research Laboratories, (2001).

Eric T. Herfindal et al., Clinical Pharmacy and Therapeutics, pp. 1068 and 1116–1117, Williams and Wilkins, (1992).

* cited by examiner

Primary Examiner—Christopher R. Tate
Assistant Examiner—Patricia A. Patten
(74) Attorney, Agent, or Firm—Foley & Lardner

(57) ABSTRACT

The invention provides a novel composition useful in the treatment of resistant bacterial infections, said composition comprising an extract obtained from *Azadiracta indica* or *Melia azadirachta* and an effective amount of an antibiotic or chemotherapuetic antibacterial drug. Further, the invention provides a method for the treatment of resistant bacterial infections. The invention also provides a process for the preparation of the composition of the invention.

18 Claims, No Drawings

COMPOSITION FOR TREATMENT OF DRUG RESISTANT BACTERIAL INFECTIONS AND A METHOD OF TREATING DRUG RESISTANT BACTERIAL INFECTIONS

FIELD OF INVENTION

The invention provides a synergistic novel composition which can be used against bacteria that have developed resistance to conventional antibiotics and other chemotherapuetic anti-microbial agents. Preferably, the invention provides a composition comprising of an herbal agent to re-sensitize the resistant bacterial strains and an antibiotic or a chemotherapuetic anti-bacterial drug to which, the bacterial strain was resistant. The invention also provides a process for the preparation of the composition.

BACKGROUND AND PRIOR ART REFERENCES OF THE INVENTION

Bacterial resistance to conventional antibiotics and other chemotherapuetic agents has been an area of serious concern in clinical practice. Sulfa-resistant gonococci were widespread 10 years after their introduction. Penicillin was introduced during 1940's. Although originally was highly susceptible, *Staphylococcus aureus* quickly developed β-lactamase mediated resistance and caused epidemics during 1950's. Semi-synthetic penicillins were developed for a broad-spectrum of anti bacterial activity. For a long time, the first member of this group, Ampicillin has been most widely prescribed drug. But, now 20–70% of *E. coli* strains are Ampicillin resistant (Beam Jr. TR 1992 on Principles of anti-infectives Use—chapter-47 in Text Book of Pharmacology, ed. Smith C M and Raynard A M, published by W. B. Saunders Company, $1^{st}$ ed., p-812–814). This phenomenon has been an important factor necessitating the development of newer anti-microbial molecules.

The bacterial resistance to an antibiotic can be of two kinds (Beam Jr. T R, 1992 on Principles of Anti-infectives Use—chapter47 in Text Book of Pharmacology, ed. Smith C M and Raynard A M, published by W. B. Saunders Company, $1^{st}$ ed., p-812–814.). The first one is called intrinsic resistance. This is a natural phenomenon and hence, all antibiotics do not exhibit activity against all sorts of bacteria but work in a selective manner. The second type is an acquired resistance. In this type, a particular bacterial species appear to be susceptible to an antibiotic initially but develops resistance over a period of time. Acquired resistance by bacteria to an antibiotic in use poses a specific problem in clinical practice, as the patients hosting such resistant organisms do not respond to the therapy.

So far, there are three well-known pathways in which, the bacteria develop resistance to any antibiotic substance. Firstly, it may produce certain enzymes, which may break down the antibiotic rendering it ineffective to work upon. For example, the penicillinase or β-lactamase produced by certain bacteria inactivates penicillin or its derivatives (Davey P G 1996 on Anti-microbial chemotherapy, chapter 7.6 in Oxford text book of medicine, vol. -I, Ed. By Weatherall D J, Ledingham J G G & Warell D A, published by Oxford University Press, $3^{rd}$ edition). Similarly, Enterobacter species work to inactivate Erythromycin by producing an esterase. In the second case, the bacteria may alter the target site. For example, Erythromycin normally latches to 50s ribosomal sub-units and inhibits the synthesis of proteins and thereby kills the bacteria. To prevent such anchoring by Erythromycin, certain bacteria are now known to modify the target site. In the last pathway, the bacteria may work to reduce the permeability of antibiotic substance by altering the structure of its own cell wall. This phenomenon can be best illustrated by *Staphylococcus epidermidis*, which inhibit the entry of erythromycin (Kapusnik-Uner J E, Sande M A & Mandell G L, 1996 on Antimicrobial agents; Tetracyclines, Chloramphenicol, Erythromycin & Miscellaneous antibacterial agents the chapter-47 in Goodman & Gilman's The Pharmacological Basis of Therapeutics, ed. By Hardman J G, Limbird E, Molinoff P B & Ruddon R W & cons. Editor Goodman Gilman A, pub. By McGraw-Hill, Health Professions Division, $9^{th}$ International edition, p-1136,1137).

Practically speaking, there can be two approaches to overcome the issue. Firstly, newer antibiotics may be developed. Alternatively, certain therapeutic additives which, can work to sensitize the bacterial species to particular antibiotic/s and render them susceptible to the present generation of antibiotics. The present invention chooses the later approach to address the problem.

In modem medicine also, there have been efforts to go by the second alternative. Development of a combination containing Amoxycillin and Clavulanic acid is the best example to illustrate such efforts. Amoxycillin is an amino-penicillin and is degraded by β-lactamase producing bacteria. Clavulanic acid was discovered to inhibit the activity of β-lactamase but is devoid of antibacterial activity of its own (Reading C & Cole M, 1977 A beta lactamase inhibiting beta lactam from *Streptomyces clavuligenus;* Antimicrob Agnets Chemother, 11, p-852–857, Reading C, Farmer T & Cole, M 1983, The Beta lactamase stability of Amoxycillin with beta lactamase inhibiting Clavulanic acid, J. Antimicrob Chemother., 11, p-27–32 & Todd P A & Benfield P 1990Amoxycillin/Clavulanic acid, an up-date of its antibacterial activity, pharmacokinetic properties & Therapeutic use, Drugs 39, p-264–307).

When Clavulanic acid was combined with amoxycillin, the antibacterial spectrum of the later was found to widen and as such, the combination is now, available for clinical applications.

On the other hand, India has one of richest heritage of traditional systems of medicine. Use of herbs in preventive and therapeutic health care has been an ageless tradition in India. Various investigators with a view to develop newer drug molecules are exploring many of these medicinal plants. Similarly, identification and development of antimicrobial molecules from medicinal plants has a long history in Indian Medicine. The earliest reports on antimicrobial activity of medicinal plants appeared way back in 1930's (Chopra RN, 1994 rpt. on therapeutic and other uses of Indian Medicinal Plants in Indigenous Drugs of India Ed. By Chopra R N, Chopra I C, Handa, K L and Kapoor L D, pub. By Academic Publishers, Calcutta, p-594–606). Since then, screening of anti-microbial compounds has continued. Many of these subjects have shown promising anti microbial activity against test strains "in-vitro" (Dhar M L, Dhar M M, Dhawan B N, Bhakuni D S, Mehrotra B N et. al. 1968–'74, Screening of Indian Plants for Biological Activity, part-I to part-V, published as series of reports in Ind. Jour. Exp. Biol., between 1968–1974). But none of these observations could ever lead to an effective development of drugs or therapeutic modalities to counter bacterial infections.

Nonetheless, synergistic effect or potentiating effect of herbs is a promising field in Ayurveda. Certain investigations on medicinal plants provide a cue that herbal drugs can be effectively utilized for identifying their additive or potentiating effects in appropriate areas. The present invention goes by this approach and seeks to explore the synergistic/potentiating or additive effects of medicinal plants to address the issue of bacterial resistance.

The neem tree, also referred as *Azadirachta indica* A. juss has been used and is known since ages for its healthcare benefits. The tree has been attributed with many therapeutic effects in various Ayurvedic texts and even the common-folk appear to have a fair understanding about its medicinal uses and therefore, they use it often, for such benefits. Mostly, the leaves, the seeds and their fixed oil portion and bark of neem are used for their medicinal activities. However, the leaves and bark are preferred for oral use in humans.

One of the common beliefs is that, various parts of neem are effective against infectious conditions. Based on these perceptions, various parts of neem have been investigated and the observations have been classified commonly as observations for antibacterial, anti-fungal and anti-viral conditions.

Similarly, neem seeds and seed oils have been examined in depth for their effect on agricultural pests. Eventually, seeds and seed oils have been picked up for development of natural pesticides. Several patents have been granted for insecticidal and fmgicidal properties of neem seeds and oil. U.S. Pat. No. 4,943,434 teaches development of insecticidal compositions employing hydrogenated extracts obtained from neem seeds (Azadirachtin). Similarly, U.S. Pat. No. 5,372,817 teaches insecticidal compositions obtained from neem oil and neem wax fractions. U.S. Pat. Nos. 5,001,146 and 5,124,346 teach storage stable pesticidal compositions containing Azadirachtin. The extract used in all these compositions is from neem seeds.

Besides the pesticide activity, neem seed oil was found to be effective against standard strains of *Bacillus subtilis*, *Salmonella typhosa* and *Salmonella paratyphi* (Jain P P, Suri R K, Deshmukh S K & Mathur K C 1987, fatty oils from oil seeds of forest origin as antibacterial agents, Ind. For, 113 (4), p-297–299). In another study, different fractions of neem leaf extract were found to be devoid of any antibacterial effect (Singh P P, Junnarkar A Y, Reddy G S & Singh K V 1987 *Azadirachta indica:* neuro-psychopharmacological and antimicrobial studies, Fitoterapia v.58 (4), p-235–238).

But the anti-viral effects of neem leaf were demonstrated against chikungunya and measles viruses by a different investigation (Gogate S S & Marathe A D 1989, Antiviral effect of neem leaf (*Azadirachta indica*) extract in chikungunya & measles viruses, Jour. Res. & Edn. In Ind. Med., 8 (1), p-1–5). The essential oils distilled from neem leaf were found to exhibit anti-fungal activity (Kher, A & Chourasia S C 1977, Antifungal activity of essential oils of three medicinal plants, Indian Drugs, December, p-41–42).

U.S. Pat. No. 5,472,700 teaches that the Azadirachtin containing extract of neem seeds, works in synergy with Bifenthrin. Such synergy was acclaimed to control acarids especially, the pyrethroid-resistant mites and also for the control of ecto-parasites on animals. Prior art also exists that, its seed extract can work in synergy with a substance known as bifenthrine against pyrethroid resistant mites and also in parasites afflicting animals. Even from this disclosure, it is only evident that, neem seed extract can intervene the biological systems of lower organisms like mites and parasites but there is no suggestion or teaching as to the use of neem extracts for intervention with the bacterial systems.

Neem leaf was also found to intervene the biological systems of certain fungi and was observed to inhibit the synthesis of aflatoxins by *Aspergillus parasiticus* (Bhatnagar D & McCormick S P (1988): The inhibitory effect of neem (*Azadirachta indica*) leaf extracts on Aflatoxin Synthesis in *Aspergillus parasiticus,* JOACS, 65(7), p-1 166–1168). Thus, several workers have proved that neem can be effectively used to inhibit the growth of certain fungi. These observations do not teach or discuss the effect of neem extracts on bacterial systems, although, there is a stray unwarranted reference to the anti-bacterial value of neem in the papers. The entire discussion of the papers is devoted to the anti-fungal or anti-pest effects of neem. In fact, the inventors of this application conducted extensive investigations to ascertain whether the neem extract has any anti-bacterial effect, but failed to identify any such anti-bacterial effect of neem extract. In this context, it is pertinent to note that, though viruses, bacteria and fungi are generally grouped as microbes or microorganisms, their biological systems are entirely different. Thus, one substance might not have a similar effect on all these three categories. For example, a drug, which can inhibit the growth of bacteria—is not capable of inhibiting of fungus or a virus. Therefore, it is never preferred to administer a fungicide substance to treat a bacterial infection or vice-versa. Further, although there exists prior-art on neem that, its extract can intervene biological systems of one particular type of fungi, it is difficult to predict whether neem extract can intervene the biological systems of every other micro-organism, like bacteria unless otherwise investigated and proven. It is also known to work against certain types of viruses and inhibit their growth, in experimental situations. However, there is no prior art disclosing the usefulness of neem extract in bacterial infections.

In another U.S. Pat. No. 5,370,873, purified extract of neem leaves was successfully demonstrated to inhibit viruses and malarial parasites. It was also disclosed that, these purified extracts inhibit the adhesion of infectious cells and cancer cells to endothelial cells. The patent is based on the principle that neem leaf products, especially its extract has anti-adhesive effect on cells. This property prevents traveling or metastasizing cells from adhering to normal cells of the body, whereby establishment of new colonies of cells is prevented. Using this principle, the patent owners have developed compositions containing neem leaf products suitable for various therapeutic applications. The active ingredient of the compositions of the patent is the neem leaf extract used with carriers and/or adjuvants. However, the teachings of this invention cannot be applied and do not aid in dealing with the problem of resistance acquired by bacteria to conventional drugs.

Thus, none of the above prior art teach or even suggest methods of overcoming resistance acquired by bacteria to conventional drug therapy. As mentioned in the foregoing sections, development of resistance by bacteria to conventional antibiotics is a problem for which no concrete solution is available. To address this problem, the inventors focussed their study on neem extract and its different properties. During their study, the inventors have observed to their surprise that neem extract can be used to address the problem of resistance developed by bacteria to conventional antibiotics. The inventors have found that neem leaf extracts are capable of re-sensitizing bacteria to drugs to which they had developed resistance. This principle has been applied in the invention to disclose novel compositions and methods of treatment.

Bacteria modify their biological systems in order to protect themselves, from the onslaught of antibiotics. As a result of these modifications, they acquire resistance and survive in their host even when the treatment with an antibiotic is on. Knowing these complex, intrinsic modifications taking place in bacteria—it would be hard to presume that, a mere admixture of two known anti-bacterial substances could do a wonder in case of resistant bacteria. Ideally, it needs an agent/substance, which can intervene these intrinsic biological mechanisms and thereby re-sensitize them to conventional antibiotics. Almost, a similar principle was employed in the discovery of Clavulanic acid—which is presently employed to treat β lactamase mediated bacterial resistance to amoxycillin. This particular drug is known as of now, to address only one type of mechanism involved in the genesis of bacterial resistance.

A given substance might affect the biological systems of any organism in many ways. It is pertinent for this invention that, such modification in the biological systems should be in a well-specified direction to address the selected issue.

The inventors chosen neem extract in a hypothetical manner and carried-out the investigations with a clear direction. The result of these inventive steps went surprisingly in favor of this hypothesis.

Right at the beginning, the hypothesis also ruled-out the usage of neem seeds considering established uses as pesticides, fungicides and such other purposes. Also, it is well established fact that, most of Azadirachtin content is deposited in the seeds as compared to other aerial parts of Neem. The inventors were concerned about the possible toxic effects of this particular constituent of neem seeds and therefore, preferred other aerial parts to seeds—for the intended investigation.

OBJECTS OF THE INVENTION

Accordingly, the main object of the invention is to provide a composition comprising an extract obtained from aerial parts of the neem tree (*Azadirachta indica* or *Melia azadirach*) and an antibiotic.

Another object is to provide a composition containing an extract obtained from the neem tree and an antibiotic to which the bacteria have developed resistance.

Yet another object is to provide a composition wherein, the role of the extract obtained from neem is to re-sensitize the bacteria which have acquired resistance to antibiotics and render them susceptible.

Still another object is to provide a method for effective utilization of neem extracts to reverse or minimize the intensity of resistance developed by bacteria to antibiotics.

Another object is to provide a method to render bacterial susceptible to the antibiotics to which they had developed resistance.

Yet another objective of invention is to provide a process for the preparation of the herbal extract for use in combination with antibiotics.

SUMMARY OF THE INVENTION

In accordance with the above and other objectives, the invention provides a novel composition useful in the treatment of resistant bacterial infections, said composition comprising an extract obtained from *Azadiracta indica* or *Melia azadirachta* and an effective mount of an antibiotic or chemotherapuetic antibacterial drug. Further, the invention provides a method for the treatment of resistant bacterial infections. The invention also provides a process for the preparation of the composition of the invention.

DETAILED DESCRIPTION OF THE INVENTION

Accordingly, the invention provides a novel synergistic composition comprising extract obtained from a neem plant, together with an effective amount of an antibiotic or chemotherapuetic antibacterial drug, said composition being useful in the treatment of resistant bacterial infections.

In an embodiment, the extract is obtained from plants selected from *Azadirachta indica* or *Melia azadirachta*. The plant chosen for this invention is *Azadirachta indica*.

In another embodiment, the extract is obtained from leaves, bark and tender twigs, or combinations thereof, preferably leaves.

In still another embodiment, the neem extract is obtained using water at its natural pH or pH adjusted from 6.0 to 6.5. The total content of bitter principles in the extract is upto 9%. Further, the extract is obtained using any one of alcohols alone or by combining with water.

In another embodiment, the amount of extract in the composition is in the range of 50–300 mg per unit dose.

In yet another embodiment, the extract re-sensitizes the resistant bacteria and renders it susceptible to antibiotics or chemotherapuetic antibacterial drugs.

In still another embodiment, the extract acts in synergy with the antibiotic or chemotherapuetic antibacterial drugs to inhibit the bacterial growth and ensure clinical recovery from infection.

In yet another embodiment, the extract exhibits selective activity with respect to the antibiotic or chemotherapuetic antibacterial drugs.

In another embodiment, the antibiotic is a member of the group comprising penicillin derivatives, quinolone derivatives and macrolide antibiotics. The penicillin derivatives comprise ampicillin, amoxycillin and piperacillin. The quinolone derivatives comprise ciprofloxacin and norfloxacin. The macrolide antibiotics comprise erythromycin and roxythromycin. The chemotherapuetic anti-bacterial drug is co-trimoxazole.

In yet another embodiment, the concentration of the antibiotic in the composition is the conventional therapeutic dosage regimen. In yet another embodiment, the concentration of chemo-therapeutic anti-bacterial drug is the conventional therapeutic dosage regimen.

In another embodiment, the composition is in different pharmaceutical dosage forms suitable for oral administration.

In another embodiment, the composition is useful for the treatment of infections caused by resistant bacterial strains of gram positive and gram negative classes.

The invention also provides a method for using an extract obtained from neem plant in combination with an effective amount of antibiotic or chemotherapuetic anti-bacterial drug for treatment of resistant bacterial infections.

As mentioned above, neem extract used in this method is obtained from the neem plants selected from *Azadirachta indica* or *Melia azadirach*. In an embodiment of the method, the neem extract is obtained from aerial parts selected from leaves, bark and tender twigs or combinations thereof. In another embodiment of the method, the extract is obtained from the leaves of *Azadirachta indica*. In still another embodiment of the method the dosage of the extract used is in the range of 50–300 mg per unit dose.

In another embodiment, the extract is used as an adjuvant to conventional antibiotics to overcome bacterial resistance.

In yet another embodiment, the antibiotic is a member of the group comprising penicillin derivatives, quinolone derivatives and macrolide antibiotics.

Further, the invention provides a method for treatment of resistant bacterial infections, said method comprising the steps of oral administration of an extract obtained from the neem plant to a subject in need thereof, in combination with an effective amount of an antibiotic or chemotherapuetic anti-bacterial drug to which the bacteria has developed resistance. The focus of the invention is not to modify the drug therapy or the dosage regimen of the conventional antibiotic or chemotherapuetic antibacterial drug treatment, but to effectively use neem extract and thereby facilitate eradication of the drug resistant infections.

In an embodiment, the extract from the neem plant and the antibiotics or chemotherapuetic antibacterial drugs are administered together as a combination or separately. In another embodiment, the extract is obtained from neem plant selected from *Azadirachta indica* and *Melia azadirach*.

In yet another embodiment, the extract from neem plant is administered before or after administration of the antibiotic, with a gap of not more than 30 minutes.

In yet another embodiment, the extract contains total bitter principles of about 9% w/w. In yet another embodiment, the amount of extract administered ranges between 100 to 600 mg per day in two or three divided doses. In yet another embodiment, the antibiotic is a member of the group comprising penicillin derivatives, quinolone derivatives and macrolide antibiotics. In yet another embodiment, the penicillin derivatives comprise ampicillin, amoxycillin and piperacillin. In another embodiment, the quinolone derivatives comprise ciprofloxacin and norfloxacin. In still another embodiment, the macrolide antibiotics comprise erythromycin and roxythromycin. In yet another embodiment, the chemotherapuetic anti-bacterial drug is co-trimoxazole. In yet another embodiment, the antibiotic or the chemotherapuetic anti-bacterial drug administered is the antibiotic or chemotherapuetic anti-bacterial drug to which the bacteria has acquired resistance.

In yet another embodiment, the extract re-sensitizes the resistant bacteria and renders it susceptible to antibiotics and chemotherapuetic antibacterial drugs. Also, the extract acts in synergy with the antibiotic or chemotherapuetic antibacterial drugs to inhibit the bacterial growth and ensure clinical recovery from infection. Further, the extract exhibits selective activity with respect to the antibiotic or chemotherapuetic antibacterial drugs used. In another embodiment, the concentration of antibiotic or chemotherapuetic antibacterial drug administered is the conventional therapeutic dosage regimen. In still another embodiment, the administration of neem extract is continued during the entire period of antibiotic therapy.

Finally, the invention provides a process for the preparation of the composition of the invention, said process comprising the steps of:

a) preparing dry coarse powder of bark, dry tender twigs and leaves of *Azadirachta indica* or *Melia azadirach*, b) preparing an aqueous extract wherein the pH of water is adjusted between 6 to 6.5 by addition of acids, c) alternatively, preparing an extract using one of alcohols or its blend with water, d) refluxing the extract by conventional methods to obtain a clear liquid, and e) concentrating and drying the extract to obtain a fine powder.

In an embodiment, the acids are selected from any of the carboxylic acids, mineral acids or a combination thereof. In yet another embodiment, the alcohols comprise ethyl alcohol, methyl alcohol, isopropyl alcohol. In another embodiment, the extraction is carried-out using a blend of one of the alcohols and water. In another embodiment, extract is obtained by a reflux technique or open pan boiling technique, or any other conventional method. In still another embodiment, the extract is concentrated by open-pan boiling technique or under vacuum or using falling film evaporators or any other conventional method. Finally, the extract is dried by tray or spray drying technique or under vacuum.

In sum, the focus of the invention is to use extracts obtained from the plants *Azadirachta indica* and *Melia azadirachta* (neem extract) in combination with antibiotics to which the bacterium causing the infection has developed resistance. The neem extract is capable of being used/administered independent (before or after) of the antibiotic in question, or the neem extract can be administered in combination or concurrent with the antibiotic as a single composition, suitable for oral administration. Thus, as used herein, reference to concurrent administration of the neem extract and the antibiotic refers to administration such that the two agents can exert their advantageous effect in combination in the subject. The inventors have observed that such administration of the neem extract renders the bacteria susceptible to the same antibiotic to which it had acquired resistance. The inventors also observed during the investigation that, in cases where the neem extract is administered independent of the antibiotic to the subject, the interval between administration of the neem extract and the antibiotic should not exceed 30 minutes. The said period of 30 minutes is not critical, but is recommended for best results. The inventors have tested the efficacy of the combination of the neem extract with antibiotics in several bacterial cultures as exemplified by the examples provided herein below and have further provided results of clinical studies, all of which indicate that the combination of neem extract with a particular antibiotic renders the bacterium in question susceptible to the antibiotic. Thus, the invention as discussed hereinbelow is yet another route to solve the problem of "acquired resistance" of bacteria.

The invention is discussed in detail hereinafter with reference to non-limiting examples and clinical studies. It should be understood that the scope of the present invention is not limited to the specific compositions or methods as described herein and that any composition or method having steps equivalent to those described herein fall within the scope of the present invention. Preparation routes of the composition of the invention and the method for combating the problem of bacterial resistance by the administration of neem extract with antibiotics is merely exemplary so as to enable one of ordinary skill in the art to use the teachings of the invention, such as the composition of the invention and use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the invention.

As such, the invention is based upon a series of investigations which, can be broadly classified into four major phases as under:

1. Phase (a): Preparation of herbal extract from any of two plant species, viz. *Azadirachta indica* and *Melia azadirachta*—which are commonly construed as Neem.
2. Phase (b): Investigation of sensitization/synergistic/potentiating effects of Neem extracts obtained through phase (a), using resistant bacterial strains isolated from clinical samples of culture.
3. Phase (c): Elaborate investigations to confirm the observations made during Phase (b).
4. Phase (d): Clinical Evaluation—to ascertain the efficacy of the new composition in human beings.

Phase (a): Preparation of Herbal Extract

One of the two-plant species viz. *Azadirachta indica* or *Melia azadirachta* (both belonging to family Meliaceae), preferably, *Azadirachta indica* were used to obtain the herbal extract employed in this invention.

Traditionally, different parts of these two plant materials are extracted into water at its natural pH. By this procedure, it was observed during experimental situations that, this procedure has limitations with reference to the chemistry of neem extract—the subject of this invention.

Both the plant subjects—*Azadirachta indica* and *Media azadirach* contain a group of substance known as, Total Bitter Compounds. From a purely a chemistry point of view, these bitter compounds can be divided into two sub-groups termed as limonoids and protolimonoids. These compounds together impart bitterness to various parts of Neem. The quantum of total bitters varies greatly, among different parts of Neem. Both these groups of Bitter compounds are widely known and are considered to play a crucial role in many of biological effects attributed to the plant species.

However, in traditional procedure of aqueous extraction—these Bitter Compounds of Neem plant are not extracted fully. When quantified, the cumulative value of Total bitters may not exceed 2.5% in such traditional extraction procedure. Also, many a time, these bitter compounds might not remain stable in the extract and undergo oxidation which can be seen by a change of colour of extract from Yellowish brown to Dark brown over a period of time.

Considering the presumed therapeutic importance of Total Bitters in Neem extract, the inventors were interested to increase these total bitter compounds further—in the final extract, upto 9%. It was also thought to be pertinent, to ensure a reliable shelf life to the aqueous extract.

It might be pertinent to refer to the contents of various process patents granted in the US and other countries related to Storage stable azadirachtin/neem oil compositions (ref.: U.S. Pat. Nos. 4,946,681, 5,001,146, 5,124,349). The inventions in these patents were aimed to develop stable pesticide/fungicide compositions. For this purpose, various process options were developed involving the usage of hydrophobic solvents/aprotic solvents.

On the contrary, the present invention seeks to employ neem extract for a defined therapeutic application and considers the aqueous extract to be a safer option for human consumption—in relation to any extracts obtained using organic solvents. At the same time, it seeks to impart a reliable shelf life to such aqueous extracts.

For this purpose, the extraction procedure was standardized by assessing various options. After few experiments, the following solvent options were found to be useful for the proposed purpose:

Water+Any of carboxylic acids (like citric acid, Oxalic acid, Phosphoric acid, acetic acid etc). The concentration of acid is adjusted to maintain a pH of water ranging between 6–6.5.

Water+Any of the Mineral acids like hydrochloric acid or sulfuric acid, the quantity of which, is adjusted to maintain a pH ranging between 6–6.5.

Nitric acid falling under the mineral acids group, was disqualified for this purpose on account of extract stability.

Water+an admixture comprising one carboxylic acid and one of the two mineral acids mentioned above.

Alternatively, the extraction may be carried-out using any one of the polar solvents like ethyl, methyl, isopropyl alcohols The extraction to provide required quantity of total bitter compounds might also be obtained by using a combination of water and any one of the alcohols.

The extract thus obtained in a weak acidic medium was employed for all the further investigations related to the invention.

The extraction procedure is summarized in the following stages:

Stage-I: Extraction Phase: For extraction purposes, the pH of was first modified to 6–6.5. This step is achieved by addition of, any one of the carboxylic acids (like Citric acid, Phosphoric acid, Oxalic acid and acetic acid) or mineral acids like hydrochloric acid or sulfuric acid or an admixture of any of these carboxylic and mineral acids to water.

Dried parts of Neem like Leaves, bark, flowers and preferably, the Neem Leaves were extracted using water having a weak acidity—as obtained from the above procedure.

Alternatively, the extraction can be carried-out, using any of the alcohol(ethyl, methyl, isopropyl) alone or in combination with water.

Stage-II: Filtration Phase: The extract is then filtered using suitable filtration media like, muslin cloth or filtration pads made of cellulose or a filter bed created by adsorbing media to obtain a clear solution.

Stage-III: The Concentration Phase: The filtrate obtained from Stage-II was subjected to concentration by distillation or by an evaporation technique employed directly or under vacuum.

Stage-IV: The drying Phase: To obtain the soluble solid constituents form the extraction—the concentrated extract was dried by a conventional tray drying or by a spray-drying technique.

Qualitative Profile of Extract:

The extract obtained as above is highly complex by its chemistry. While, there could be large number secondary and primary plant metabolites, an effort was made to define an outline of its qualitative profile which, is produced as below:

| Tests | Specification | Standard Test Procedure |
|---|---|---|
| Description | Yellowish brown color powder having characteristic odor | Visual and olfactory test |
| Identification | Positive for Nimbin and nimbidin | In-house test procedure |
| pH(1% w/v suspension) | 4.0 to 6.0 | Indian Pharmacopoeia 1996, pg A-95 |
| Ash content (total) | Not more than 20% | Indian Pharmacopoeia 1996, pg A-54 |
| Loss on drying (at 85° C.) | Not more than 5%(w/w) | Indian Pharmacopoeia 1996, pg A-89 |
| Alcohol soluble extractive | Not more than 40%(w/w) | Indian Pharmacopoeia 1996, pg A-53 |
| Total Bitters | Up to 9% | In house test procedure |

Besides various chemical constituents, the extract described above contains a group of substances termed as Total Bitters and their quantitative value may go upto 9% (depending upon the natural variations in the raw material used for the purpose) in the final extract. Literature suggests that, these compounds comprise limonoids and protolimonoids. The extract was also characterized by qualitative presence of nimbin, and nimbidin in combination or in isolation. The specific character of the aforesaid extract is also that, it contains nimbin and nimbidin only in traces and generally, not amenable to quantification. This very specific feature of the extract renders it safe for human use.

The product thus, obtained is labeled as Neem Extract for further experiments and hereinafter referred to as NE.

These experiments were conducted in two distinct phases. During Phase—(b), a limited number of bacterial species isolated from wider clinical samples were used and the investigations were carried-out to check to the sensitization role of NE against a wider range of antibiotics. Once, the spectrum of its sensitization activity was identified, more focused investigations were done on a larger number of culture isolates representing a limited number of bacterial species and a limited number of antibiotic substances. Both preliminary and confirmation experiments were conducted in a hospital scenario—to study the effect of Neem Extract (NE) on practically resistant bacteria as occur in clinical infections.

Phase—(b) (Preliminary In-vitro investigations on NE):

For this purpose, the clinical samples referred for routine culture and sensitivity tests were monitored. The. cultures of all bacterial species/strains exhibiting resistance to commonly used antibiotics—were preserved for the purpose of investigations. The resistant bacterial cultures used in the investigation, included β-*haemolytic streptococci, Corynaebacterium diphetheriae,* Gram Negative enteric bacilli, *Staphylococcus aureus, Escherichia coli, Klebseilla pneumoniae, Proteus vulgaris,* Enterobacter species, *Salmonella senftenberg* etc.

The Selection of resistant Strains & Quantification of Resistance:

During preliminary phase of investigations, bacterial resistance to Ampicillin/Amoxycillin, Ciprofloxacin, Co-trimoxazole, Erythromycin, Cefalexin, Gentamicin, Amikacin and such other antibiotics was taken into account. Once the organism was found to be resistant to one or more of these antibiotics, further experiments were conducted to quantify the intensity of bacterial resistance to each of these antibiotics. This was done by estimation of the Minimum Inhibitory Concentration (MIC) and Minimum Bactericidal Concentration (MBC) on the selected isolates by a Broth Macro Dilution Test.

While conducting these tests, the guidelines given by the National committee of Clinical Laboratory Standards 1995 protocols were employed. Cation Supplemented Mueller Hinton Broth was used as medium for all organisms excepting for β *haemolytic streptococci* for which, Todd Hewit's Broth was used as medium.

The following concentrations of antibiotics were tested to determine MIC and MBC.

Ampicillin ($\mu$g /ml)
   0.5, 1,2, 4, 8, 16, 32, 64 for β-*haemolytic streptococci*
   2, 4, 8, 16, 32, 64, 128, 256 for gram-negative *bacilli*

Ciprofloxacin ($\mu$g/ml)
   0.5, 1,2, 4, 8, 16 β-*haemolytic streptococci*
   4,8, 16, 32, 64, 128, 256 for gram-negative *bacilli*

Co-trimoxazole (Sulpharnethoxazole/Trimethoprim/$\mu$g/$\mu$g per ml)
   0.5/9.5, 1.0/19, 4.0/76, 8.0/152, 16/304, 32/608

Erythromycin (used only for β-*haemolytic streptococci* and *Staphylococcus aureus*) in $\mu$g/ml 0.25, 0.5, 1, 2, 4, 8, 16, 32, 64, 128, 256

A minimum inhibitory concentration is the lowest level of antibiotic needed to cause an inhibition to bacterial growth in culture medium whereas, the minimum bactericidal concentration is the lowest concentration of antibiotic to achieve a 100% killing of bacteria. Thus, these two values are the practical indices of intensity of bacterial resistance to a given antibiotic. On the other hand, a break-even point of any antibiotic indicates the attainable blood levels after an administration of full dose, in human/animal body. Thus, this point indicates the practical dosage of administering any given antibiotic effectively and beyond this point, even if an antibiotic is found to act effectively in experimental situation—such dose cannot be administered in a clinical situation. Therefore, an effective antibiotic should exhibit activity against given bacterial cultures at this concentration otherwise; it becomes a useless compound for that particular infection.

Therefore, it is logical to conclude that, NE is expected to sensitize the resistant bacteria to a given antibiotic and make it, susceptible to antibiotic at a break-even point concentration in the culture medium.

Investigations on Neem Extract (NE):

Since all the study isolates are resistant to the concerned antibiotics, each antibiotic is taken at its breakpoint concentration, (the highest serum concentration of that particular antibiotic reached after the maximum therapeutic dose in-vivo). The break points for various antibiotics are as follows:

| 1. | Ampicillin/Amoxacillin | 16 µg/ml |
| 2. | Co-trimoxazole | 4/76 µg/ml |
| 3. | Cefalexin | 18 µg/ml |
| 4. | Ciprofloxacin | 4 µg/ml |
| 5. | Erythromycin | 4 µg/ml |

Preparation of Neem Extract: Stock solution of neem extract (1 mg/ml) was prepared, filtered and autoclaved. It was used in 4 concentrations—1000 µg/ml; 500 µg/ml; 250 µg/ml; 125 µg/ml.

A set of four tubes with variable concentrations of the extract is prepared and to each of these tubes, the break point concentration of antibiotics is added. Now, these sets are inoculated with the study isolate in the same manner as per the broth dilution procedure. A set of six controls is inoculated with each isolate—in parallel with the main experiment.

1. Only medium
2. Only antibiotic solution
3. Medium and antibiotic solution with inoculum
4. Medium and inoculum
5. Only Neem extract at 250 µg/ml
6. Medium with Neem Extract and inoculum Reading the test All the tests and control tubes are observed for visible turbidity of growth first. Since all the study isolates were earlier confirmed to be resistant to the antibiotics, the bacterial growth is expected at the breakpoint concentration of the antibiotic. Any reduction in the turbidity as compared to the control tube no. 3 is noted as a possible additive or synergistic effect of the neem extract with the antibiotic. In absence of such effect, the tubes may show growth matching with the control no. 4.

In case of a positive result, further sub-culturing was taken up, on solid media for colony counts with a calibrated loop. The colony counts could be noted by a semi quantitative method as 101 to $10^5$ CFU/ml (Colony forming units). This is finally expressed as the percentage of killing as compared to the colony count obtained with control no. 4. Usually control tubes no. 3, 4 and 6 had similar colony counts.

Observations on NE during In-vitro investigations:

1. At the end of test procedure, it was observed that, there was no bacterial growth in control tube nos. 1, 2 and 5. This observation implies that, the culture medium and other substances used in the study were properly sterilized and rule-out the possibilities of misleading results.
2. It was observed that, there was a confluent growth of inoculated culture in control tube-no. 4. This implies that, the bacterial strain used in the study is viable and thrive-upon a nutrient medium.
3. During the investigation, it was observed that, there was a confluent growth of resistant bacteria in the control tube no. 3 in which, the antibiotic was added in a concentration of Break-even point. This observation implies that, the concerned bacteria are resistant to the antibiotic employed in that culture tube.
4. Bacterial growth was also confluent in the control tube no. 6. This indicates that Neem extract does not kill bacteria on its own.
5. Contrary to these observations, the bacterial growth was inhibited in the test tubes containing the NE and the antibiotic. This observation when read with observations of tubes 3 and 4, suggest the NE works against the bacterial resistance to the antibiotic and renders it, susceptible to the drug.

The above observations clearly suggest that, NE does not possess any inherent anti-bacterial activity. However, it sensitizes surprisingly, a resistant bacterial strain and renders it susceptible to well-known antibiotic drugs.

These observations are recorded in the Provisional Indian Patent application filed in Indian Patent Office on Sep. 17, 1999 (application No 1260/DEL/99 dtd Sep. 17, 1999).

Phase (c): Confirmatory In-vitro Investigations on NE

To confirm the dramatic effect of NE on antibiotic resistant bacterial strains—as observed in this invention, further experiments were conducted in a focused manner.

For this purpose, 206 strains of bacterial cultures which, were diagnosed to be resistant to antibiotics originating from various clinical samples such as sputum, throat swabs, endotracheal tube tips, surgical wounds, urine culture samples etc. Two kinds of investigations were carried-out using these bacterial isolates—using an Agar Dilution Method of Sensitivity testing.

i) To ascertain whether, NE can work as an antibacterial substance on its own. For this purpose, a stock-solution of NE was prepared and was sterilized as described in the preliminary experiments.

ii) This stock-solution was dispensed into the culture medium (Mueller Hinton Agar) so as to provide while; the medium was in liquid form. Four different concentrations of NE, viz. 125 µg/mL, 250 µg/mL, 500 µg/mL, and 1000 µg/mL, were employed to evaluate the effect at different dose levels.

iii) This medium was poured into petri dishes and allowed to solidify. Resistant cultures were inoculated on to these plates and after incubation for 48 hours, the growth patterns were assessed.

iv) The experiments were run in triplicate, for each concentration—as per standard practices of microbiological testing procedures.

v) It was observed that, NE did not inhibit the growth of any of these 206 cultures and there was confluent growth of each of the resistant bacteria even in a plate containing highest concentration of NE.

The first of part of the investigations thus, confirmed that NE does not possess any inherent antibacterial activity. Subsequently, its additive/synergistic effect along with antibiotics was assessed. For this purpose, the following steps were followed:

i) The culture medium (Mueller Hinton Agar) was melted and distributed into a number of test tubes.

ii) The stock solution of NE was dispensed into these test tubes in four different concentrations viz. 125 µg/mL, 250 µg/mL, 500 µg/mL, and 1000 µg/mL.

iii) In the same medium, one of the antibiotics under investigation was also added so as to provide a variable concentration (at break-even point concentration) as described below:

| | |
|---|---|
| Ampicillin: | 16 µg/mL |
| Cephalexin: | 32 µg/mL |
| Ciprofloxacin: | 4 µg/mL |
| Erythromycin: | 4 µg/mL |
| Gentamicin: | 8 µg/mL |
| Piperacillin: | 16 µg/mL | iv) The culture medium containing NE extract+the antibiotic were poured into petri dishes and allowed to solidify.

v) The resistant bacterial strains were inoculated onto these plates, incubated for 48 hours and the growth patterns were studied on each plate.

vi) These investigations revealed that, NE inhibits the growth patterns of different bacterial strains in a selective manner—working in synergy with the antibiotic.

vii) Such inhibition was observed to be bacteria specific as well as antibiotic specific. It does not sensitize all bacteriae to all antibiotics in universal manner. But it exhibits a specific behavior as regards its re-sensitization effect on -bacterial strains resistant to antibiotics.

viii) The novelty of investigation lies there, in such very specificity—which is illustrated under different examples. In both phase (b) and phase (c) investigations, neem extract did not show any sensitization effect on bacteria resistant to aminoglycoside group of antibiotics (for example gentamicin, amikacin etc) or those resistant to cephalosporin group of antibiotics (such as Cephelexin, Cefotaxime etc) or to tetracycline group of antibiotics. Based on these negative observations, the inventors opined that NE might riot work in synergy with these antibiotics.

Clinical Studies on NE to examine its Effects in Human Subjects:

In order to confirm the aforesaid sensitization effects of NE in human subjects, a brief clinical study was undertaken as follows:

i) 24 human subjects suffering from non-responding infections were enrolled into this study to examine whether addition of NE could alter clinical and bacteriological picture of these cases. Out of them, only 22 cases came-for a follow-up and therefore, these 22 cases were taken as evaluable cases.

ii) Of these 22 cases, 15 persons were suffering from infection of external ulcers and delayed wound healing due to continued infection. Rest of 7 persons was suffering from respiratory infections by bacteria resistant to commonly used antibiotics.

iii) The culture and sensitivity test done at the time of their inclusion in the study, confirmed the type of infecting bacteria, their resistance patterns.

iv) After this testing, these patients were administered NE provided in form of Tablets (containing 100 mg of NE per tablet) and they were asked to use them at a dose of one tablet twice a day.

v) They were also advised to use one of the antibiotics—to which, the bacterial resistance was established in culture & sensitivity testing.

vi) The combination regime of treatment (comprising NE+Antibiotic) was continued for a period of 1–3 weeks depending upon the intensity and chronicity of infection.

vii) These patients were followed-up for clinical improvement and after completion therapy for prescribed duration, another round of culture and sensitivity tests were performed—to examine—whether the infecting bacteria is eliminated or not.

viii) The clinical and bacteriological response was graded in order to assess the efficacy of NE for the proposed clinical purpose.

ix) At the end of study, it was observed that, there was a complete clinical and bacteriological and clinical response in 15 cases, a partial response in 3 cases. In rest of 4 cases, there was no improvement seen even after 3 weeks of therapy.

A careful analysis of these results also revealed that, NE works in a selective manner with reference to its sensitization effect. The novelty of this invention lies in this kind of specificity—which is discussed in the following examples.

EXAMPLE -1

*Escherichia coli* was isolated from a wound infection and this culture was found to be resistant to Ciprofloxacin by a standard disc diffusion technique in routine culture and sensitivity test. In further experiments, it was noted that, the minimum inhibitory concentration (MIC) was 8 µg/ml and minimum bactericidal concentration (MBC) goes to be 64 µg/ml concentration. However, the break-even point for this antibiotic is 4 µg/ml concentration. In the subsequent experiment, 4 µg/ml of Ciprofloxacin was combined with four different concentrations of NE i.e. 125 µg/ml, 250 µg/ml, 500 µg/ml and 1000 µg/ml respectively.

It was observed that, Ciprofloxacin combined with NE could attain a 100% bactericidal effect at its break point concentration. To compare these observations, NE and Ciprofloxacin were added individually in control tubes and the bacterial growth was observed to be unhindered in both the controls.

These observations indicate that, the NE contributes to reversal of resistance and at the same time, it is not capable of inhibiting/killing a resistant bacteria on its own.

EXAMPLE -2

*Escherishia coli* was isolated from endotracheal catheter tip culture and this culture was found to be resistant to Ciprofloxacin by a standard disc diffusion technique in routine culture and sensitivity test. In further experiments, it was noted that the minimum inhibitory concentration (MIC) was 32 µg/ml and minimum bactericidal concentration (MBC) was noted to be >128 µg/ml concentration. However, the break-even point for this antibiotic is 4 μg/ml concentration. In the subsequent experiment, 4 μg/ml of Ciprofloxacin was combined with four different concentrations of NE i.e. 125 μg/ml, 250 μg/ml, 500 μg/ml and 1000 μg/ml respectively.

It was observed that Ciprofloxacin combined with NE could attain a 40% bactericidal effect at its break point concentration. To compare these observations NE and Ciprofloxacin were added individually in control tubes and the bacterial growth was observed to be unhindered in both the controls.

These observations imply that the NE contributes to reversal of resistance but is incapable of inhibiting/killing resistant bacteria on its own.

In both the above examples, it is seen that, though *Escherichia coli* was responding to the combination of neem extract—the degree of response is varied. These variations are mainly, on account of intrinsic variations in the biological systems of different bacterial strains belonging to the same species.

EXAMPLE-3

A strain of *Klebsiella pneumoniae* was isolated from a non-healing burn wound. This strain was found to be resistant to Ciprofloxacin by the disc diffusion technique. In subsequent test the MIC was noted to be 16 μg/ml and MBC was noted to be >64 μg/ml as against 4 μg/ml of break even point. Contrary to this, it was observed that, Ciprofloxacin achieved a 99% killing (in 4 μg/ml concentration) when used in combination with NE in 4 different concentrations. The results were reproducible in all the concentrations i.e. 1000 μg/ml, 500 μg/ml, 250 μg/ml and 125 μg/ml. These results infer that Neem Extract reverses the bacterial resistance to the Ciprofloxacin in this case also. In this experiment also, NE did not exhibit any antibacterial effect per-se as observed in the control tubes containing NE alone.

This particular organism was also found to be resistant to Co-trimoxazole when tested by a routine disc diffusion technique. By a macro tube dilution method, the MIC for this chemotherapeutic agent was observed to be 8/152 μg/ml and MBC was noted to be >16/304 μg/ml. Contrary to these observations, NE was observed to partially reverse the bacterial resistance to Co-trimoxazole and the drug was able to achieve a 50% killing under the test conditions. This effect was found to be uniform for all the concentrations of NE used in the study.

EXAMPLE-4

A strain of *Klebsiella pneumoniae* was isolated from a wound swab culture. This isolate was observed to be resistant to Ciprofloxacin by disc diffusion technique. The MIC and MBC of Ciprofloxacin for this strain were observed to be 32 μg/ml and >128 μg/ml respectively as against 4 μg/ml of break-even point concentration. However, when Ciprofloxacin was added to NE, a 90% killing was achieved in the culture tubes. This effect was found to be uniform at all four concentrations of the test compound used in this study. NE does not exhibit any degree of bactericidal effect per-se against this resistant strain also as observed in the control tubes.

The above organism was also found to be resistant to Co-trimoxazole. The known break-even point for this chemotherapuetic combination is 4/76 μg/μg/ml. In further experiment the MIC and MBC were identified to be 8/152 μg/μg/ml, 16/304 μg/μg/ml respectively. As against these observations, Co-trimoxazole became effective in its break-even concentrations i.e. 4/76 μg/μg/ml when used in combination with NE and was able to achieve a 90% killing in the culture tubes. Such reversal of resistance to Co-trimoxazole was found to be uniform in all the four concentrations of the NE used in the study.

EXAMPLE-5

*Klebsiella pneumoniae* was isolated from Endotracheal Catheter Tip culture and this culture was found to be resistant to Ciprofloxacin by a standard disc diffusion technique in routine culture and sensitivity test. In further experiments, it was noted that the minimum inhibitory concentration (MIC) was 32 μg/ml and minimum bactericidal concentration (MBC) goes to >128μg/ml concentration. However, the break-even point for this antibiotic is 4 μg/ml concentration. In the subsequent experiment, 4 μg/ml of Ciprofloxacin was combined with four different concentrations of NE i.e. 125 μg/ml, 250 μg/ml, 500 μg/ml and 1000 μg/ml respectively.

It was observed that, Ciprofloxacin combined with NE could attain a 90% bactericidal effect at its break-even point concentration. To compare these observations, NE and Ciprofloxacin were added individually in control tubes and the bacterial growth was observed to be unhindered in both the controls.

These observations imply that the NE contributes to reversal of resistance but is not capable of inhibiting/killing resistant bacteria on its own.

EXAMPLE-6

*Klebsiella pneumoniae* was isolated from Endotracheal Catheter tip culture and this culture was found to be resistant to Ciprofloxacin by a standard disc diffusion technique in routine culture and sensitivity test. In further experiments, it was noted that the minimum inhibitory concentration (MIC) was 32 μg/ml and minimum bactericidal concentration (MBC) was noted to be >128 μg/ml. However, the break-even point for this antibiotic is 4 μg/ml concentration. In the subsequent experiment, 4 μg/ml of Ciprofloxacin was combined with four different concentrations of NE i.e. 125 μg/ml, 250 μg/ml, 500 μg/ml and 1000 μg/ml respectively It was observed that Ciprofloxacin combined with NE could attain 80% bactericidal effect at its break point concentration. To compare these observations NE and Ciprofloxacin were added individually in control tubes and the bacterial growth was observed to be unhindered in both the controls.

These observations imply that the NE contributes to reversal of resistance but is not effective in inhibiting/killing resistant bacteria on its own.

EXAMPLE-7

*Klebsiella pneumoniae* was isolated from endotracheal catheter tip culture and this culture was found to be resistant to Ciprofloxacin by a standard disc diffusion technique in routine culture and sensitivity test. In further experiments, it was noted that the minimum inhibitory concentration (MIC) was 32 µg/ml and minimum bactericidal concentration (MBC) was noted to be >128 µg/ml concentration. However, the break-even point for this antibiotic is 4 µg/ml concentration. In the subsequent experiment, 4 µg/ml of Ciprofloxacin was combined with four different concentrations of NE i.e. 125 µg/ml, 250 µg/ml, 500 µg/ml and 1000 µg/ml respectively.

It was observed that, Ciprofloxacin combined with NE could attain a 50% bactericidal effect at its break point concentration. To compare these observations, NE and Ciprofloxacin were added individually in control tubes and the bacterial growth was observed to be unhindered in both the controls.

These observations imply that the NE contributes to reversal of resistance but is incapable of inhibiting/killing resistant bacteria on its own.

In examples 5, 6 and 7 it is evident that, *Klebsiella penumoniae* obtained from clinical samples of similar nature. However, their response rate to addition of Neem Extract to Ciprofloxacin was variable. Such kind of variations in response rate might be attributed to the intrinsic variations of a complex biological system.

EXAMPLE-8

β-*haemolytic streptococci* were isolated from a throat swab culture and this culture was found to be resistant to Erythromycin by a standard disc diffusion technique in routine culture and sensitivity test. In further experiments, it was noted that, the minimum inhibitory concentration (MIC) was 64 µg/ml and minimum bactericidal concentration (MBC) goes to >128 µg/ml concentration. However, the break-even point for this antibiotic is 4 µg/ml concentration. In the subsequent experiment, 4 µg/ml of Erythromycin was combined with four different concentrations of NE i.e. 125 µg/ml, 250 µg/ml, 500 µg/ml and 1000 µg/ml respectively.

It was observed that, Erythromycin combined with 3 different concentrations (125, 250 and 500 µg/ml) of NE could attain a 100% bactericidal effect at its break-even point concentration. However, at 1000 µg/ml of NE, this effect was noted to be little low and 99% bactericidal effect was exhibited by erythromycin. To compare these observations, NE and Erythromycin were added individually in control tubes and the bacterial growth was observed to be unhindered in both the controls.

These observations imply that the NE contributes to reversal of resistance but is not capable of inhibiting/killing resistant bacteria on its own.

EXAMPLE-9

β-*haemolytic streptococci* were isolated from a sputum culture and this culture was found to be resistant to Erythromycin by a standard disc diffusion technique in routine culture and sensitivity test. In further experiments, it was noted that the minimum inhibitory concentration (MIC) was 32 µg/ml and minimum bactericidal concentration (MBC) goes to >128 µg/ml concentration. However, the break-even point for this antibiotic is 4 µg/ml concentration.

In the subsequent experiment, it was observed that, Erythromycin combined with NE could attain a 99% bactericidal effect at its break even point concentration. This effect was observed with NE at 250 µg/ml and 125 µg/ml concentrations more specifically. When the concentration of NE was increased to 500 µg/ml or 1000 µg/ml only 50% killing was achieved by Erythromycin at its break-even point. This observation infers that, NE reverses the bacterial resistance only, at selected concentrations.

To compare these observations, NE and Erythromycin were added individually in control tubes and the bacterial growth was observed to be unhindered in both the controls.

These observations imply that the NE contributes to reversal of resistance but is incapable of inhibiting/killing resistant bacteria on its own.

EXAMPLE-10

Enterobacter spp. was isolated from Endotracheal Catheter Tip culture and this culture was found to be resistant to Ciprofloxacin by a standard disc diffusion technique in routine culture and sensitivity test. In further experiments, it was noted that the minimum inhibitory concentration (MIC) was 32 µg/ml and minimum bactericidal concentration (MBC) goes to >128 µg/ml concentration. However, the break-even point for this antibiotic is 4 µg/ml concentration. In the subsequent experiment, 4 µg/ml of Ciprofloxacin was combined with four different concentrations of NE i.e. 125 µg/ml, 250 µg/ml, 500 µg/ml and 1000 µg/ml respectively.

It was observed that Ciprofloxacin combined with NE could attain 80% bactericidal effect at its break point concentration. To compare these observations NE and Ciprofloxacin were added individually in control tubes and the bacterial growth was observed to be unhindered in both the controls.

These observations imply that the NE contributes to reversal of resistance but is incapable of inhibiting/killing resistant bacteria on its own.

EXAMPLE-11

Enterobacter spp. was isolated from Endotracheal catheter tip culture and this culture was found to be resistant to Ciprofloxacin by a standard disc diffusion technique in routine culture and sensitivity test. In further experiments, it was noted that the minimum inhibitory concentration (MIC) was 32 µg/ml and minimum bactericidal concentration (MBC) was noted to be >128 µg/ml concentration. However, the break-even point for this antibiotic is 4 µg/ml concentration. In the subsequent experiment, 4 µg/ml of Ciprofloxacin was combined with four different concentrations of NE i.e. 125 µg/ml, 250 µg/ml, 500 µg/ml and 1000 µg/ml respectively.

It was observed that Ciprofloxacin combined with NE could attain a 50% bactericidal effect at its break point concentration. To compare these observations NE and Ciprofloxacin were added individually in control tubes and the bacterial growth was observed to be unhindered in both the controls.

These observations imply that the NE contributes to reversal of resistance but is incapable of inhibiting/killing resistant bacteria on its own.

EXAMPLE-12

A strain of *Staphylococcus aureus* was isolated from a non-healing burn wound swab culture. This strain was found to be resistant to Ciprofloxacin by the disc diffusion technique. In subsequent test, the MIC was noted to be 32 µg/ml and MBC was noted to be >128 µg/ml as against 4 µg/ml of break even point. Contrary to this, it was observed that Ciprofloxacin achieved an 80% killing (in 4 µg/ml concentration) when used in combination with 250 µg/ml and 125 µg/ml NE. However, these results were not reproducible in other concentrations and there was only a 20% bactericidal effect at 1000 µg/ml, 500 µg/ml of NE. These results infer that NE reverses the bacterial resistance to Ciprofloxacin in this case, only 25 when used in defined concentrations. In this experiment also, NE did not exhibit any antibacterial effect per-se as observed in the control tubes containing NE alone.

The organism was further found to be resistant to Ampicillin when tested by a routine disc diffusion technique. By a macro tube dilution method the MIC for this antibiotic was observed to be 64 µg/ml and MBC was noted to be more than >128 µg/ml. Contrary to these observations, NE was observed to reverse the bacterial resistance to Ampicillin and the drug was able to achieve 80% killing under the test conditions. This effect was found to be uniform for all the concentrations of NE used in the study.

This particular organism was also found to be resistant to Erythromycin when tested by a routine disc diffusion technique. By a macro tube dilution method the MIC for this antibiotic was observed to be 128 µg/ml and MBC was noted to be more than >256 µg/ml. Contrary to these observations, NE was observed to reverse the bacterial resistance to Ampicillin and the drug was able to achieve a 70% killing under the test conditions. This effect was found to be uniform for all the concentrations of NE used in the study.

EXAMPLE-13

A strain of *Salmonella senftenberg* was isolated from a burn wound swab culture. This isolate was observed to be resistant to Ciprofloxacin by disc diffusion technique. The MIC and MBC of Ciprofloxacin for this strain were observed to be 32 µg/ml and >128 µg/ml respectively as against 4 µg/ml of Break even point concentration. However, when Ciprofloxacin was added to 1000 µg/ml NE, a 50% killing was achieved in the Culture tubes. With 500 µg/ml NE, this effect was somewhat low and at other concentrations this effect was not found. NE does not exhibit any degree of bactericidal effect per-se against this resistant strain also as observed in the control tubes.

The above organism was also found to be resistant to Co-trimoxazole. The break-even point for this chemotherapeutic combination is 4/76 µg/ml. In further experiments, the MIC and MBC were identified to be 8/152 µg/µg/ml and 16/304 µg/µg/ml respectively. As against these observations, Co-trimoxazole became effective to some extent when used in combination with different concentration of NE and was able to achieve a 60% killing in the culture tubes. Such reversal of resistance to Co-trimoxazole was found to be uniform in all the four concentrations of the test compounds used in the study.

EXAMPLE-14

During confirmatory investigations on NE, 102 cultures of *Staphylococcus aureus* were employed to ascertain its sensitization effect. These cultures were obtained various clinical samples, such as sputum, non-healing infected wounds, throat swabs etc. All these cultures were confirmed to be resistant to ampicillin, Cephalexin, Ciprofloxacin, Erythromycin, Gentamicin.

When NE alone was used in the culture medium for these cultures, it could not inhibit their growth in any fashion and there was a confluent growth of each culture even at highest concentration of NE (1000 µg/mL). This phenomenon shows that, NE doesn't have a direct antibacterial effect per-se.

When NE was added along with the antibiotic to which, the individual strains were found to be resistant the following results were obtained:

| Name of Antibiotic to which, resistance was seen: | No. of Cultures Tested | Growth Patterns after addition of NE at different Concentrations | | | | | | | |
|---|---|---|---|---|---|---|---|---|---|
| | | 125 µg/mL | | 250 µg/mL | | 500 µg/mL | | 1000 µg/mL | |
| | | +++ | --- | +++ | --- | +++ | --- | +++ | --- |
| Ampicillin | 102 | 34 | 68 | 29 | 73 | 26 | 76 | 20 | 82 |
| Cephalexin | 102 | 81 | 21 | 81 | 21 | 81 | 21 | 81 | 21 |
| Ciprofloxacin | 101 | 83 | 18 | 83 | 18 | 83 | 18 | 83 | 18 |
| Erythromycin | 102 | 72 | 30 | 66 | 36 | 61 | 41 | 51 | 51 |
| Gentamicin | 102 | 89 | 13 | 88 | 14 | 88 | 14 | 88 | 14 |

+++ Shows the growth of organism and --- show the inhibition of growth of organism.

The results shown in above table clearly suggest that, after addition of NE, the *Staph. aureus* cultures were sensitized significantly entailing in their increased susceptibility. As a result, out of 102 cultures, NE+Ampicillin could inhibit the growth of 68 cultures at a concentration of 125 µg/mL. Such inhibition increased further, with increasing concentrations of NE in the culture with a break-even Point concentration of Ampicillin (16 µg/mL).

Similarly, NE could sensitize 50% of clinical strains to erythromycin and this antibiotic represents the class of macrolide antibiotics.

However, in case of other two antibiotics, its sensitization effect is not so marked and NE could sensitize only a small number of resistant strains employed in the investigation.

EXAMPLE-15

Under the same series of investigations, sensitization effect of NE was evaluated on resistant isolates of *Klebsiella pneumoniae*. A total of 41 strains were tested for this organism and all of them were initially resistant to Ampicillin and Ciprofloxacin. NE also, did not show any inhibitory effect per-se—against these 41 isolates of *Klebsiella pneumoniae*. The following table shows the additive/synergistic/sensitization effect of NE as evidenced in this example:

| Name of Antibiotic to which, resistance was seen: | No. of Cultures Tested | Growth Patterns after addition of NE at different Concentrations | | | | | | |
|---|---|---|---|---|---|---|---|---|
| | | 125 µg/mL | | 250 µg/mL | | 500 µg/mL | | 1000 µg/mL |
| | | +++ | --- | +++ | --- | +++ | --- | +++ | --- |
| Ampicillin | 41 | 17 | 24 | 17 | 24 | 17 | 24 | 17 | 24 |
| Ciprofloxacin | 41 | 38 | 3 | 38 | 3 | 38 | 3 | 38 | 3 |

+++ Shows the growth of organism and --- show the inhibition of growth of organism.

In this particular organism also, NE could sensitize the resistant organism only to Ampicillin and such effect was found to be less effective in case of Ciprofloxacin resistance. This example also suggests the specificity of NE in the reversal/minimization of bacterial resistance to antibiotics. In case of *Klebsiella pneumoniae*, NE selectively sensitizes it, to Ampicillin.

EXAMPLE-16

When NE was examined for its sensitization role on 37 resistant strains of *Escherichia coli*, the effect was found to be more marked with Ciprofloxacin and was minimal in case of Ampicillin. The following table shows this phenomenon:

| Name of Antibiotic to which, resistance was seen: | No. of Cultures Tested | Growth Patterns after addition of NE at different Concentrations | | | | | | |
|---|---|---|---|---|---|---|---|---|
| | | 125 µg/mL | | 250 µg/mL | | 500 µg/mL | | 1000 µg/mL |
| | | +++ | --- | +++ | --- | +++ | --- | +++ | --- |
| Ampicillin | 37 | 31 | 6 | 31 | 6 | 31 | 6 | 31 | 6 |
| Ciprofloxacin | 37 | 19 | 18 | 19 | 18 | 19 | 18 | 19 | 18 |

+++ Shows the growth of organism and --- show the inhibition of growth of organism.

| Name of Antibiotic to which, resistance was seen: | No. of Cultures Tested | Growth Patterns after addition of NE at different Concentrations | | | | | | |
|---|---|---|---|---|---|---|---|---|
| | | 125 µg/mL | | 250 µg/mL | | 500 µg/mL | | 1000 µg/mL |
| | | +++ | --- | +++ | --- | +++ | --- | +++ | --- |
| Piperacillin | 16 | 3 | 13 | 3 | 13 | 3 | 13 | 3 | 13 |
| Ciprofloxacin | 16 | 7 | 9 | 7 | 9 | 7 | 9 | 7 | 9 |

+++ Shows the growth of organism and --- show the inhibition of growth of organism In this experiment also, NE could not inhibit the growth of bacterial strains even when used in its highest concentration (1000 μg/mL). But the same extract could achieve a satisfactory rate of bacterial inhibition in synergy with Ciprofloxacin. This example shows that, resistant strains of E. coli could be sensitized to Ciprofloxacin.

EXAMPLE-17

Piperacillin represents penicillin derivative class of broad-spectrum antibiotics like Ampicillin. During last few years, the drug has been a choice in the treatment of Pseudomonas infections. However, resistance of Pseudomonas species to this new generation penicillin derivative is not uncommon.

During the investigations on NE, 16 strains of *Pseudomonas aerugenosa* were identified to be resistant to this particular antibiotic. Of these 16, 13 isolates could be sensitized to this particular antibiotic. In the same organism, the resistance to Ciprofloxacin could also be controlled effectively and the growth could be inhibited effectively, by addition of NE. These results are tabulated below:

EXAMPLE-18

The sensitization effect of NE was also examined on *Proteus mirabilis* strains resistant to Penicillin derivatives and quinolone derivative antibiotics. The results of this testing are provided in the following table.

| Name of Antibiotic to which, resistance was seen: | No. of Cultures Tested | Growth Patterns after addition of NE at different Concentrations | | | | | | |
|---|---|---|---|---|---|---|---|---|
| | | 125 μg/mL | | 250 μg/mL | | 500 μg/mL | | 1000 μg/mL | |
| | | +++ | --- | +++ | --- | +++ | --- | +++ | --- |
| Ampicillin | 10 | 7 | 3 | 7 | 3 | 7 | 3 | 7 | 3 |
| Ciprofloxacin | 16 | 7 | 9 | 7 | 9 | 7 | 9 | 7 | 9 |

+++ Shows the growth of organism and --- show the inhibition of growth of organism In this organism, the test substance has shown significant sensitization to Ciprofloxacin and in case of Ampicillin the activity is somewhat, low.

EXAMPLE-19

To ascertain the bacterial sensitization effect of NE (which is proven in experimental scenario) a clinical study was conducted on 24 cases. After drops-out, there were 22 evaluable cases in this study. The results of this study are enumerated below:

Material & Methods:

The samples of NE were prepared in form of film coated tablets (containing 100 of NE per tablet). Patients suffering from respiratory and/or surgical infections were enrolled into the study after a due consideration to inclusion and exclusion criteria:

Inclusion Criteria
  Patients of both sexes aged above 16 years.
  Patients with history of respiratory/surgical infections were included.
  Patients with a history of infections not responding to one or more of the three specific antibiotics viz. Ciprofloxacin, Ampicillin and erythromycin/roxythromycin were included in the study.

Exclusion Criteria
  Patients diagnosed to be of fresh infections were excluded
  Pregnant women were excluded
  Cases resistant to other antibiotics were excluded
  Patients suffering from systemic conditions like diabetes were excluded.

Method of Study:

A sample of Sputum/throat swab or pus was collected on enrollment for culture and sensitivity test. After establishing the causative organism and the resistance/sensitivity patterns. If the culture and sensitivity report indicated a significant resistance to one or more of the selected antibiotics, viz. Ciprofloxacin (representing quinolone derivatives), Erythromycin/roxythromycin (representing macrolide antibiotics) and Ampicillin/amoxycillin (representing penicillin derivatives)—the following therapeutic regime was instituted:

1. One of the above antibiotic, (to which the bacterial resistance is established) in a standard dosage regimen.
2. Addition of NE tablets (containing 100 mg of Neem Extract) at a dose of one tablet twice a day
3. In case of surgical infections, local care of infected in a standard regimen.

In case of respiratory infections, no other medication was administered during the investigations.

The above treatment schedule was continued for 1–3 weeks, depending upon the chronicity of infection.

Subjective response to treatment was elicited once in every week. As and when a significant relief was noted, the culture and sensitivity test was repeated, to correlate the clinical response to bacteriological response.

Parameters of Evaluation
  1. Subjective response to treatment.
  2. Bacteriological response as evidenced from Culture and Sensitivity testing.

Grading of Response
  1. Grade—II Response: Cases cleared from subjective symptoms and when the culture was found to be sterile after 48 hours incubation—were considered as Complete response. These cases were labeled as Grade—II response.
  2. Grade—I Response: Cases with a distinct subjective response but the culture test was positive for bacterial infection.
  3. Grade—0 Response: Cases with no clinical or bacteriological response—after addition of NE to the antibiotic.

Results:

A total of 24 patients were enrolled into the study and two cases did not go for follow-up investigations and hence, were treated as dropout cases. Out-of 22 evaluable cases, there were 15 cases of surgical infections and 7 cases of respiratory infection. All these patients received some or the other antibiotic therapy for a minimum of 15 days before enrollment into the study and therefore, were clinically considered to be of resistant infections.

The Sex and age distribution of patients is shown in Table—I and Table-II respectively.

TABLE I

Showing Sex Distribution among patients

| | No. of cases: | | |
|---|---|---|---|
| Type of Infection | Male: | Female: | Total |
| Surgical Infections | 12 | 3 | 15 |
| Respiratory Infection | 4 | 3 | 7 |
| Totals: | 16 | 6 | 22 |

TABLE II

Showing the Age distribution in the Study Population.

| | No. of Cases in Age groups | | | | |
|---|---|---|---|---|---|
| Type of Infection | 16–25 yrs. | 26–35 yrs. | 36–45 yrs. | 46 yrs. & above | Totals |
| Surgical Infections | 1 | 8 | 5 | 1 | 15 |
| Respiratory Infections | 3 | 3 | 1 | — | 7 |
| Totals: | 4 | 11 | 6 | 1 | 22 |

Table—III shows the infecting organism isolated during cultures of clinical specimen. Bacterial resistance patterns, to the selected three antibiotic substances, at the time of enrollment.

TABLE III

Showing the Organism Isolated in Cultures of Clinical Specimen

| | Source Clinical Specimen: | | |
|---|---|---|---|
| Name of Organism: | Pus Cultures | Sputum Cultures | Total: |
| *Staphylococcus aureus* | 9 | 5 | 14 |
| Gram + *ve cocci* | 1 | — | 1 |
| *Staph. aureus* + Psuedomonas | 2 | — | 2 |
| *Staph. aureus* + *E. coli* | 3 | 1 | 4 |
| Streptococcus + Psuedomonas | — | 1 | 1 |
| Mixed Infections: (Totals) | 5 | 2 | 7 |
| Grand Totals: | 15 | 7 | 22 |

TABLE IV

IV shows the resistance patterns of the clinical isolates to the selected antibiotics.

| | No. of Cultures resistant to: | | | |
|---|---|---|---|---|
| Name of Organism: | Ciprofloxacin | Roxy-thromycin | Ampicillin/Amoxycillin | Total |
| *Staphylococcus aureus* | 8 | 4 | 2 | 14 |
| Gram + *ve cocci* | — | — | 1 | 1 |
| *Staph. aureus* + Psuedomonas | 2 | — | — | 2 |
| *Staph. aureus* + *E. coli* | 2 | — | 2 | 4 |
| Streptococcus + Psuedomonas | — | — | 1 | 1 |
| Mixed Infections: (Totals) | 4 | — | 3 | 7 |
| Grand Totals: | 12 | 4 | 5 | |

TABLE V

Sensitization Effect of NE on Ciprofloxacin Resistant Infections:

| | Infecting | No. of Cases | | | |
|---|---|---|---|---|---|
| Type of Infection | Organism | Gr-0 | Gr.-I | Gr.-II | Totals |
| Respiratory Infections | *Staphylococcus aureus* | — | — | 4 | 4 |
| | Mixed Infection | — | — | 1 | 1 |
| Totals of Respiratory Infections Resistant to Ciprofloxacin | — | — | — | 5 | 5 |
| Surgical Infections | *Staphylococcus aureus* | 1 | — | 3 | 4 |
| | Mixed Infections | 1 | 1 | 1 | 3 |
| Totals of Surgical Infections Resistant to Ciprofloxacin | — | 2 | 1 | 4 | 7 |
| Total no. Of cases Resistant to Ciprofloxacin | — | 2 | 1 | 9 | 12 |

TABLE VI

Sensitization Effect of NE on Ampicillin Resistant Infections:

| | | No. of Cases | | | |
|---|---|---|---|---|---|
| Type of Infection | Infecting Organism | Gr-0 | Gr.-I | Gr.-II | Totals |
| Respiratory Infections | *Staphylococcus aureus* | — | — | — | — |
| | Gram + ve cocci | 1 | — | — | 1 |
| | Mixed Infections | — | 1 | 1 | 2 |
| Surgical Infections | *Staphylococcus aureus* | — | — | 2 | 2 |
| | Mixed Infections | — | — | 1 | 1 |
| Total cases Resistant to Ampicillin | — | 1 | 1 | 4 | 6 |

Sensitization effect of NE on Roxythromycin resistant bacteria is shown in table-VII.

TABLE VII

| | Infecting | No. of Cases | | | |
|---|---|---|---|---|---|
| Type of Infection | Organism | Gr-0 | Gr.-I | Gr.-II | Totals |
| Respiratory Infections | *Staphylococcus aureus* | — | 1 | — | 1 |

TABLE VII-continued

| Type of Infection | Infecting Organism | No. of Cases | | | |
|---|---|---|---|---|---|
| | | Gr-0 | Gr.-I | Gr.-II | Totals |
| Surgical Infections | Staphylococcus aureus | 1 | — | 2 | 3 |
| Total Cases of Roxythromycin Resistance | — | 1 | 1 | 2 | 4 |

TABLE VIII

Showing Overall Response:

| Name of Antibiotic | Response Patterns (no. of cases) | | | |
|---|---|---|---|---|
| | Grade-0 | Grade-1 | Grade-II | Totals: |
| Ciprofloxacin | 2 | 1 | 9 | 12 |
| Ampicillin | 1 | 1 | 4 | 6 |
| Roxythromycin | 1 | 1 | 2 | 4 |
| Totals: | 4 | 3 | 15 | 22 |

As seen from above tables, there were a total of 22 cases in this assessment. Of them, 15 cases had surgical infections and 7 cases had respiratory infections. Among the 15 cases of surgical infections, *Staphylococcus aureus* was found in 9 cases, mixed infections in 5 cases and one case had Gram+ve cocci as infecting organism.

Among the 7 cases of Respiratory infections also, *Staph. aureus* predominated with 5 cases and rest of 2 cases had mixed infections.

Ciprofloxacin resistance & Role of Neem Extract (NE):

The resistance patterns suggest that, 8 isolates of *Staphylococcus aureus* were resistant to Ciprofloxacin. Of these 8 cases, NE—DR could sensitize the infecting organism in 7 cases. In one case—there was no clinical or bacteriological response to the addition of test drug. These observations indicate that, in a majority of cases, DRF-11198 (neem extract) was able to sensitize *Staphylococcus aureus* and to subscribe to the clinical recovery with Ciprofloxacin.

Similarly, there were 4 cases of mixed infections resistant to Ciprofloxacin. Of them, there was an effective sensitization of infecting organisms in 2 cases, a partial response in One case while, the last did not show any kind of response.

In all, the resistance to Ciprofloxacin could be reverted by test substance- in 9 cases. A partial remission could be achieved one case and there was no practical effect of the test drug in Two cases.

It is also pertinent to note that, during Phase-II of in-vitro evaluation, NE could not effectively sensitize *Staph. aureus* against Ciprofloxacin. However, the clinical study proves that, the test substance works effectively—for this purpose. This kind of difference between human situations and experimental situations are possible—due to complex mechanisms of biological functioning.

In case of an "in-vitro" experiment it is only the drug that works against the microbial growth. On the other hand, in a clinical scenario—the human biological system is also working against the infection and Neem Extract was adding its value as a sensitizing the organism to the antibiotic drug being administered. Therefore, the observations in the clinical study hold a greater value in this context.

Ampicillin Resistance & Role of NE:

The resistance patterns in the study suggest that, there were two isolates of *Staphylococcus aureus*, which were resistant to Ampicillin/amoxycillin, involved in surgical infections. Both these isolates were sensitized to, and the cases responded to treatment with Ampicillin. Similarly, out of 3 mixed infections resistant to Ampicillin, 2 cases responded completely and there was a partial remission in one case. Apart from these five cultures, there was one case diagnosed be of Gram+ve cocci and this case did not respond to therapy with NE in any manner.

Thus, it may be summed-up that, out-of 6 bacterial isolates resistant to Ampicillin, there was a complete sensitization of 4 cultures, a partial remission of resistance in one case. One culture did not show any sensitization response to the test drug.

Macrolide Resistance & Role of NE.

Roxythromycin is the latest introduction in this category and with its introduction, the use of earlier drug, erythromycin is not much in clinical use. However, bacteria developed resistance to this drug as well. In the present study, 4 strains of *Staphylococcus aureus* were isolated. NE could sensitize 2 of these strains and there was complete clinical and bacteriological response to Roxythromycin. There was one case with a partial remission and one did not respond to its addition.

The above clinical results are in conformity with the observations made during initial phases of investigations.

We claim:

1. A composition for the treatment of resistant bacterial infections, the composition comprising pharmaceutically effective amounts of (i) an extract obtained from the aerial parts of the leaves, stem, or tender twigs of a neem plant, and (ii) an antibiotic selected from a penicillin derivative, a quinolone derivative and a macrolide antibiotic to which the bacterium has developed resistance, wherein the extract comprises water, alcohol, or both.

2. A composition as claimed in claim 1 wherein the neem plant is *Azadirachta indica*.

3. A composition as claimed in claim 1 wherein the neem plant is *Melia azadirachta*.

4. A composition as claimed in claim 1 wherein the extract is obtained from aerial parts selected from leaves, bark, tender twigs or combinations thereof.

5. A composition as claimed in claim 1 wherein the extract is obtained from the leaves of the neem plant.

6. A composition as claimed in claim 1 wherein the extract is obtained using water at its natural pH or pH adjusted from 6.0 to 6.5.

7. A composition as claimed in claim 1 wherein the total content of bitter principles in the extract is up to 9%.

8. A composition as in claim 1 wherein the extract is obtained using any one of alcohols alone or by combining with water.

9. A composition as claimed in claim 1 wherein the amount of extract in the composition is in the range of 50–300 mg per unit dose.

10. A composition as claimed in claim 1 wherein the extract re-sensitizes the resistant bacterium and renders it susceptible to the antibiotic.

11. A composition as claimed in claim 1 wherein the extract acts in synergy with the antibiotic to inhibit bacterial growth.

12. A composition as claimed in claim 1 wherein the penicillin derivatives comprise ampicillin, amoxycillin and piperacillin.

13. A composition as claimed in claim 1 wherein the quinolone derivatives comprise ciprofloxacin and norfloxacin.

14. A composition as claimed in claim 1 wherein the macrolide antibiotics comprise erythromycin and roxythromycin.

15. A composition as claimed in claim 1 wherein the anti-bacterial drug is co-trimoxazole.

16. A composition as claimed in claim 1 wherein the concentration of the antibiotic in the composition is the conventional therapeutic dosage regimen.

17. A composition as claimed in claim 1 wherein the composition is in different pharmaceutical dosage forms suitable for oral administration.

18. A composition as claimed in claim 1 wherein the composition is used for the treatment of infections caused by resistant bacterial strains of gram positive and gram negative classes.

* * * * *